(12) United States Patent
Moon et al.

(10) Patent No.: US 6,903,199 B2
(45) Date of Patent: Jun. 7, 2005

(54) CROSSLINKED AMIDE DERIVATIVES OF HYALURONIC ACID AND MANUFACTURING METHOD THEREOF

(75) Inventors: Tae-seok Moon, Kyoungki-Do (KR); Jae-young Lee, Seoul (KR); Jin-hoon Kim, Daejeon-Si (KR); Kyu-beom Han, Daejeon-Si (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 10/398,065

(22) PCT Filed: Oct. 10, 2001

(86) PCT No.: PCT/KR01/01687

§ 371 (c)(1),
(2), (4) Date: Apr. 18, 2003

(87) PCT Pub. No.: WO02/30990

PCT Pub. Date: Apr. 18, 2002

(65) Prior Publication Data

US 2004/0014960 A1 Jan. 22, 2004

(30) Foreign Application Priority Data

Oct. 10, 2000 (KR) .......................................... 2000-59443

(51) Int. Cl.⁷ ........................... C08B 37/08; C08B 37/00
(52) U.S. Cl. ........................... 536/20; 536/53; 536/55.1; 536/124

(58) Field of Search ........................... 536/53, 124, 55.1, 536/20

(56) References Cited

U.S. PATENT DOCUMENTS

| | | | |
|---|---|---|---|
| 4,582,865 A | | 4/1986 | Balazs et al. |
| 4,713,448 A | | 12/1987 | Balazs et al. |
| 5,017,229 A | | 5/1991 | Burns et al. |
| 5,760,200 A | * | 6/1998 | Miller et al. .................. 536/21 |
| 5,874,417 A | * | 2/1999 | Prestwich et al. ............ 514/54 |

FOREIGN PATENT DOCUMENTS

WO    WO 86/00912    2/1986

* cited by examiner

*Primary Examiner*—James O. Wilson
*Assistant Examiner*—Ganapathy Krishnan
(74) *Attorney, Agent, or Firm*—Swanson & Bratschun, L.L.C.

(57) ABSTRACT

The present invention relates to water-insoluble, crosslinked amide derivatives of hyaluronic acid and manufacturing method thereof, where the amide derivatives of hyaluronic acid are characterized by crosslinking, of polymer or oligomer having two or more amine groups, with hyaluronic acid or its hyaluronate salts through amidation reaction. The water-insoluble, crosslinked amide derivatives of hyaluronic acid according to the present invention may be diversely used for prevention of adhesion after surgical operation, correction of facial wrinkles, dermal augmentation, tissue engineering, osteoarthritic viscosupplement etc.

19 Claims, 5 Drawing Sheets

CROSSLINKED AMIDE DERIVATIVES OF HYALURONIC ACID AND MANUFACTURING METHOD THEREOF

RELATED APPLICATIONS

This application is a 35 U.S.C. § 371 national phase application of PCT/KR01/01687 (WO 02/30990) filed on Oct. 10, 2001, entitled "Crosslinked Amide Derivatives of Hyaluronic Acid and Manufacturing Method Thereof," which claims priority to Korean Application No. 2000/59443, filed Oct. 10, 2000, which is incorporated herein by reference in its entirety.

TECHNICAL FIELD

The present invention relates to crosslinked amide derivatives of hyaluronic acid and manufacturing methods thereof, more particularly, a water-insoluble, crosslinked amide derivatives of hyaluronic acid characterized by crosslinking of polymer or oligomer having two or more amine groups, with hyaluronic acid or its hyaluronate salts through amidation reaction.

BACKGROUND ART

Hyaluronic acid (hereinafter abbreviated 'HA') is a biopolymeric material where repeat unit comprising N-acetyl-D-glucosamine and D-glucuronic acid is linearly repeated in connection, which polymer plentifully exists in vitreous humor, synovial fluid, connective tissues etc. In this specification, the term 'HA' means hyaluronic acid and any of its hyaluronate salts. Hyaluronate salts according to the present invention include but not limited to inorganic salts such as sodium hyaluronate and potassium hyaluronate etc. and organic salts such as tetrabutylammonium hyaluronate etc. Preferable hyaluronate salt of HA according to the present invention is sodium hyaluronate.

HA derivatives have been developed in diverse uses for prevention of adhesion after surgical operation, correction of facial wrinkles, dermal augmentation, tissue engineering, osteoarthritic viscosupplement etc. HA derivatives may largely be classified by water solubility into water-soluble derivatives and water-insoluble derivatives. In the case of water-insoluble derivatives, manufacturing methods of those may largely be thought in two ways: one is to react HA with a compound having one functional group to combine this compound with linear chain of HA while the other is to react HA with a compound having two or more functional groups to make crosslinked HA.

There have been reported in several literature various examples to have synthesized many crosslinked, water-insoluble HA derivatives by using compounds such as divinylsulfone, bisepoxide, bishalide, formaldehyde, etc. having two functional groups.

There have been reported in U.S. Pat. No. 4,582,865 to have used divinylsulfone in order to crosslink HA and in U.S. Pat. No. 4,713,448 to have carried out crosslinking reaction by using formaldehyde. And there has been reported in PCT Patent Publication WO86/00912 an example to have used compound containing epoxy groups in order to crosslink various polysaccharides containing carboxyl group.

There is a report that water solubility of HA derivatives is decreased if carboxyl group of HA is activated in aqueous solution by using EDC (1-ethyl-3-(3-dimethylaminopropyl) carbodiimide hydrochloride) and then reacted with compounds containing one amine group to form amide bond (see U.S. Pat. No. 4,937,270). And there is an example to have crosslinked HA with various polyanionic polysaccharides using EDC (see U.S. Pat. No. 5,017,229).

DISCLOSURE OF INVENTION

It is accordingly an object of the present invention to provide water-insoluble, crosslinked amide derivatives of HA characterized by crosslinking polymer or oligomer having two or more amine groups with HA by way of amidation reaction.

Another object of the present invention is to provide manufacturing method of such water-insoluble, crosslinked amide derivatives of HA as above.

The present invention relates to crosslinked amide derivatives of HA and manufacturing method thereof. The above derivatives may be those crosslinked through amidation reaction from polymer or oligomer having two or more amine groups and having various molecular weights together with HA having various molecular weights. Preferably, the above polymer or oligomer may be polycationic polymer or oligomer. Crosslinked amide derivatives of HA according to the present invention are good in viscoelasticity, so they may be applied in diverse uses. Also crosslinked amide derivatives of HA according to the present invention may have characteristics of such as sponge or rubber.

Particularly, the present invention have features that faster reaction rate and higher yield can be obtained by reacting the polycationic polymer or oligomer having two or more amine groups with HA having carboxylate group, so the above polycationic polymer or oligomer and the above HA are close to each other by electrostatic attraction between the amine groups and carboxyl groups. Because the polycationic polymer or oligomer having two or more amine groups and the HA do not form the ionic bonds but form the covalent bonds by amidation reaction, the crosslinked amide derivatives of HA according to the present invention are biomaterials which resist various conditions of living bodies, i.e., high salt concentrations, low pH etc. And those may be said to be new biomaterials having quite different properties from existing water-insoluble HA derivatives crosslinked by using EDC.

Features of water-insoluble, crosslinked amide derivatives of HA according to the present invention are that these are new bio-materials having overcome demerit of existing water-insoluble HA derivatives to be easily decomposed in living body and easily dissolved under harsh condition such as acidic condition etc. as well as these are biologically acceptable material of excellent properties showing high viscoelasticity.

The present invention provides water-insoluble, crosslinked amide derivatives of HA in that the polycationic polymer or oligomer having two or more amine groups and HA are crosslinked each other by amidation reaction. The polymer or oligomer having two or more amine groups means that it has two or more amine groups per polymer or oligomer molecule. Preferably the present invention provides water-insoluble, crosslinked amide derivatives of HA characterized in that the polymer or oligomer contains amine groups which can accept protons so that have positive charges under acidic or neutral condition and the polymer or oligomer having amine groups reacts with carboxyl groups of HA under the existence of carboxyl group activating agent to produce water-insoluble, crosslinked amide derivatives of HA according to the present invention by promoting the amidation reaction induced by electrostatic attraction between the amine groups of the polymer or oligomer and carboxyl groups of the HA. Preferably, the present invention provides water-insoluble, crosslinked amide derivatives of HA characterized in that the ratio of the carboxyl groups of the HA versus the amine groups of the polycationic polymer or oligomer is 1:0.01 to 100 in the reaction mixture. More preferably, the present invention provides water-insoluble, crosslinked amide derivatives of HA characterized in that the polymer or oligomer having two or more amine groups reacts with carboxyl group of HA under the existence of carboxyl group activating agent to produce water-insoluble, crosslinked amide derivatives of HA according to the present invention by amidation reaction. More preferably, the present invention provides water-insoluble, crosslinked amide derivatives of HA characterized in that the amidation reaction is carried out under acidic or neutral condition, the polymer or oligomer is polycationic polymer or oligomer charged positively by protonating the amine group in the polymer or oligomer, so the amine groups of the polycationic polymer or oligomer and the carboxyl group of the HA promote the amidation reaction by using the electrostatic attraction between the amine groups of the polymer or oligomer and carboxyl groups of the HA.

The present invention also provides manufacturing method of water-insoluble, crosslinked amide derivatives of HA characterized in that the method comprising a step of reacting polymer or oligomer having two or more amine groups with HA. More preferably, the present invention provides manufacturing method of water-insoluble, crosslinked amide derivatives of HA characterized in that polymer or oligomer having amine groups which can accept protons so that have positive charges under acidic or neutral condition and the amine groups of the polymer or oligomer react with the carboxyl groups of the HA. More preferably, the present invention provides manufacturing method of water-insoluble, crosslinked amide derivatives of HA characterized in that the ratio of the carboxyl group of the HA versus the amine group of the polymer or oligomer is 1:0.01 to 100 in the reaction mixture. More preferably, the present invention provides manufacturing method of water-insoluble, crosslinked amide derivatives of HA characterized in that the amidation reaction is carried out under acidic or neutral condition, the polymer or oligomer is polycationic polymer or oligomer charged positively by protonating the amine group in the polymer or oligomer, so the amine groups of the polymer or oligomer react with the carboxyl groups of the HA.

Examples of the above polymer or oligomer having two or more amine groups are natural materials having two or more amine groups, synthetic materials synthesized by using these natural materials, and polymer or oligomer derivatives thereof. The molecular weights of the above polymers are preferably about 3,000 to 10,000,000 while the molecular weights of the above oligomers are about 300 to 3,000.

More preferably, the present invention provides manufacturing method of water-insoluble, crosslinked amide derivatives of HA characterized in that the method comprising steps of: mixing the HA aqueous solution with the polymer or oligomer aqueous solution having two or more amine groups to induce electrostatic attraction between the HA and the polymer or oligomer; reacting the two functional groups existing close to each other, i.e. carboxyl group of the HA and amine group of the polymer or oligomer to produce water-insoluble bio-materials; washing with water and acid solution etc.; isolating the refined material; and drying the material.

The manufacturing method according to the present invention has some features of easy reaction, simple separation process and no needs of toxic, organic solvent.

Examples of the carboxyl group activating agent added to the amidation reaction to activate the carboxyl group are carbodiimides. Preferably, the above carbodiimide may be selected from the group comprising compounds easily soluble in water such as EDC (1-ethyl-3-(3-dimethylaminopropyl)carbodiimide hydrochloride), 1-alkyl-3-(3-dimethylaminopropyl) carbodiimides having structure similar to EDC, ETC (1-ethyl-3-(3-(trimethylammonio)propyl)carbodiimide), CMC (1-cyclohexyl-3-(2-morpholinoethyl)carbodiimide).

More preferably, auxiliary agent to the above amidation reaction may be added optionally. Materials soluble in water, capable of forming active ester, may all be used as auxiliary agent to the above amidation reaction. Examples of the auxiliary agent may be selected from the group comprising NHS (N-hydroxysuccinimide), HOBt (1-hydroxybenzotriazole), HOOBt (3,4-dihydro-3-hydroxy-4-oxo-1,2,3-benzo triazine), HOAt (1-hydroxy-7-azabenzotriazole), Sulfo-NHS (N-hydroxysulfosuccinimide) etc.

In case of using the auxiliary agent such as NHS in comparison to case of not using it, there was decreased formation of by-product such as N-acylurea while there was no significant difference for material property of obtained crosslinked amide derivatives of HA.

To activate carboxyl group, EDC may be added in 0.0001 to 100 mg/ml and NHS may be added in 0 to 100 mg/ml in the preferable examples of the present invention.

It is preferable that the molecular weight of HA used for crosslinked amide derivatives of HA and manufacturing method thereof according to the present invention may be 10,000 to 10,000,000 and the concentration of HA may be 0.01 to 100 mg/ml.

Examples of the polymer or oligomer having two or more amine groups in the manufacturing method according to the present invention may be selected from the group comprising chitosan, chitosan derivatives, deacetylated HA, deacetylated HA derivatives, polyethylene glycol or protein or peptide having two or more reactable amine groups which can accept proton, etc.

It is preferable that the polymer or oligomer having two or more amine groups used for the crosslinked amide derivatives of HA and its manufacturing method according to the present invention may be substance soluble in aqueous solution of pH 2 to 8.

It is preferable that the solvent using in the amidation reaction according to the present invention, may be water, aqueous buffer solution, etc. but not limited to these. It is preferable that the temperature of the amidation reaction according to the present invention is 0 to 40° C., and more particularly room temperature. It is preferable that the pH of the amidation reaction according to the present invention may be 2 to 8, and more particularly 4 to 6. The amidation reaction time according to the present invention is 0.5 to 20 hours, more particularly about 2 hours.

Water-insoluble, crosslinked amide derivatives of HA according to the present invention may be made to have form of gel, membrane, bead, mesh, etc.

For each reaction in the specification, product may be separated and/or refined from the reaction system according to usual method known to the art. Examples of the separation and/or refinement may be selected from distillation under atmospheric or vacuum distillation, recrystallization, column chromatography, ion exchange chromatography, gel chromatography, affinity chromatography, thin layer chromatography, phase separation, solvent extraction, washing, etc. Refining may be carried out after each reaction or a series of reaction.

The reagents and the start materials required for the amide derivative synthesis according to the present invention may either be easily prepared by the methods disclosed in the known literature, above-described methods or be purchased from many manufacturers all over the world.

MODES FOR CARRYING OUT THE INVENTION

The present invention will become more fully understood from the examples given hereinbelow and the accompanying tables and drawings, which are given by way of illustration only, and thus are not limitative of the present invention.

EXAMPLE 1

Preparation of Amide Derivatives of HA Crosslinked with Chitosan 1.25 mg/ml of aqueous solution of sodium hyaluronate (mol. wt. $\geq 2,000,000$) and 0.625 mg/ml of aqueous solution of chitosan-HCl were prepared. The above aqueous solution of chitosan-HCl was added while the above aqueous solution of sodium hyaluronate was being stirred. Chitosan-hyaluronate was precipitated after the aqueous solution of chitosan-HCl had been added. pH became 4 to 5 after complete mixing of the two solutions. EDC and NHS were slowly added to the above mixed solution with concentrations according to the following Table 1 while stirring well. Reaction was carried out for two hours at 25° C. after this addition.

TABLE 1

| Specimen group | EDC Concentration [mg/ml] | [EDC]/[COOH in HA] | NHS Concentration [mg/ml] | [NHS]/[COOH in HA] |
|---|---|---|---|---|
| A | 0 | 0 | 0 | 0 |
| B | 0.2 | 1/3 | 0.24 | 2/3 |
| C | 0.4 | 2/3 | 0.48 | 4/3 |
| D | 0.6 | 1 | 0.72 | 2 |
| E | 1.2 | 2 | 1.44 | 4 |

The sample not added of EDC and NHS in Table 1, namely, the sample where chitosan and HA have been precipitated in form of ionic bond, may be dissolved in water under condition of high salt concentration or low pH. 1N HCl was added slowly to the above mixed solution until this sample (group A in Table 1) is completely dissolved. About 30 min. were required for this addition where about 3 ml of 1 N HCl was required for the above mixed solution 100 ml to be dissolved completely. Remainder samples (added of EDC and NHS, groups B, C, D, and E in Table 1) were also treated under same condition, and unreacted chitosan and HA which were simply precipitated in ionic bond form were removed from the amide derivatives of HA crosslinked with chitosan through amidation reaction. Remainder part not dissolved even after the above acid treatment was washed with abundant water to completely remove unreacted EDC or NHS and by-products of these after which this remaining portion was vacuum dried at 25° C. Water-insoluble, amide derivatives of HA crosslinked with chitosan could be obtained through the above procedure. The more EDC and NHS were added for the reaction, the larger quantity of final product could be obtained. The following resultant percentages are the yields of the amide derivatives of HA crosslinked with chitosan which were obtained for respective specimen groups: 49% from Group B, 58% from Group C, 71% from Group D, and 77% from Group E.

EXAMPLE 2

Preparation of Amide Derivatives of EA Crosslinked with Chitosan 1.25 mg/ml of aqueous solution of sodium hyaluronate (mol. wt. $\leq 2,000,000$) and 0.625 mg/ml of aqueous solution of chitosan-HCl were prepared. Water-insoluble amide derivatives of HA crosslinked with chitosan were obtained by reacting the above two materials and then by refining as described in Example 1. The more EDC and NHS were added for the reaction, the larger quantity of final product was able to be obtained as described in Example 1. The following resultant percentages are the yields of the amide derivatives of HA crosslinked with chitosan which were obtained for respective specimen groups: 53% from Group B-1, 62% from Group C-1, 69% from Group D-1, and 77% from Group E-1.

EXAMPLE 3

A Test of Resistance to Acid and High Salt Concentration and a Confirmation of Amide Formation in the Amide Derivatives of HA Crosslinked with Chitosan 1.25 mg/ml of aqueous solution of sodium hyaluronate and 0.625 mg/ml of aqueous solution of chitosan-HCl were prepared. The above aqueous solution of chitosan-HCl was added while the above aqueous solution of sodium hyaluronate was being stirred. Chitosan-hyaluronate was precipitated after the aqueous solution of chitosan-HCl had been added. pH became 4 to 5 after complete mixing of the two solutions. EDC and NHS were slowly added to the above mixed solution with concentrations according to the following Table 2 while stirring well. Reaction was carried out for two hours at 25° C. after the addition.

If it is not treated by acid after reaction but is washed with water several times to refine product and then vacuum dried, chitosan-HA complex precipitated by ionic bond also remains in final product in mixed situation. Products were obtained by acid treatment and refinement through same procedure as described in Example 1 in case where EDC and NHS were added (samples A, B and C in Table 2) while chitosan-HA complex precipitated by ionic bond was obtained by refining without acid treatment in case where EDC and NHS were not added (sample D in Table 2). Then, these were vacuum dried and were dispersed in 0.1 N HCl (aq.) so that each sample becomes 0.02% (w/v), and then respective times elapsed to dissolve completely were measured, which are shown in Table 2.

TABLE 2

| Sample | EDC [mg/ml] | NHS [mg/ml] | Time elapsed to dissolve completely |
|---|---|---|---|
| A | 1.2 | 1.44 | More than 120 hrs |
| B | 0.6 | 0.72 | More than 120 hrs |
| C | 0.2 | 0.24 | 80 hrs |
| D | 0 | 0 | Less than 1 hr |

Each sample was dispersed in 1 N HCl (aq.) to become 1% (w/v) in order to observe behavior in 1 N HCl (aq.) for Table 2 samples and then each sample solution was stirred for 24 hrs after which it was observed to record the result in Table 3.

TABLE 3

| Sample | Status of each sample (1% (w/v)) after leaving it in 1 N HCl (aq.) for 24 hrs |
|---|---|
| A | Opaque small particles have not been dissolved but are dispersed in whole solution |
| B | Solution has been formed where opaque gel and transparent gel coexist |
| C | Very fine particles are observed while generally transparent solution has been formed |
| D | Transparent solution has been formed by complete dissolution |

The Table 2 samples were added while stirring to become 1% (w/v) in 1 N NaCl (aq.) in order to examine endurance of Table 2 samples to high salt concentration. Transparent solution was made as the precipitate was completely dissolved in 30 min. only for case of sample D while other samples maintained their respective forms over ten days. This result means that samples A, B and C did not form complex by ionic bond, but were crosslinked by covalent bond between chitosan and HA.

Infrared spectroscopy spectra for samples A through D which have been vacuum dried after preparing and refining as described in Example 3 are presented in FIGS. 1 to 4. It was shown that the peak around 1728.6 $cm^{-1}$ by C=O stretch of carboxyl group of HA having made a salt with chitosan amine that has accepted proton is relatively decreased as the crosslinking reaction is progressed (cf. FIGS. 1 to 4). It was shown that the peak around 1557.5 $cm^{-1}$ owing to deformation of primary amine of chitosan which has accepted proton is relatively decreased as the crosslinking reaction is progressed so that it remains only as a shoulder form in the case of sample A (cf. FIGS. 1 to 4). This result shows that quantity of amine group and carboxyl group which were forming ionic bond (salt form) is decreased with their reaction and it coincides with the fact that the peak around 1600.6 $cm^{-1}$ by C=O stretch of amide is relatively increased as the crosslinking reaction is progressed (cf. FIGS. 1 to 4). As it has been generally known that hydrogen bonding is increased as the crosslinking is progressed wherewith the peak by C=O stretch of amide is moved down to a lower wavenumber, now the fact that the peak appeared at wavenumber (1600.6 $cm^{-1}$) that is lower than ordinary amide peak location (around 1660 $cm^{-1}$, J. Bioactive & Compatible Polymers, 9, 429–447 (1994)) coincides with the fact that material according to the present invention has been crosslinked as shown by the test of resistance to acid and high salt concentration. These data confirm that these derivatives of HA according to the present invention have been crosslinked by amide formation. Formation of ester (1745 to 1760 $cm^{-1}$) or anhydride of carboxylic acid (1800 $cm^{-1}$), which can occur as side reaction was not observed on spectrums (Silverstein et al., Spectrometric Identification of Organic Compounds, pp. 122 to 124, John Wiley and Sons, New York (1981)). Formation of N-acylurea (1700 $cm^{-1}$) that is a by-product that may be made when using EDC was not also observed on spectrums (see U.S. Pat. No. 5,527,893).

Figure 1:
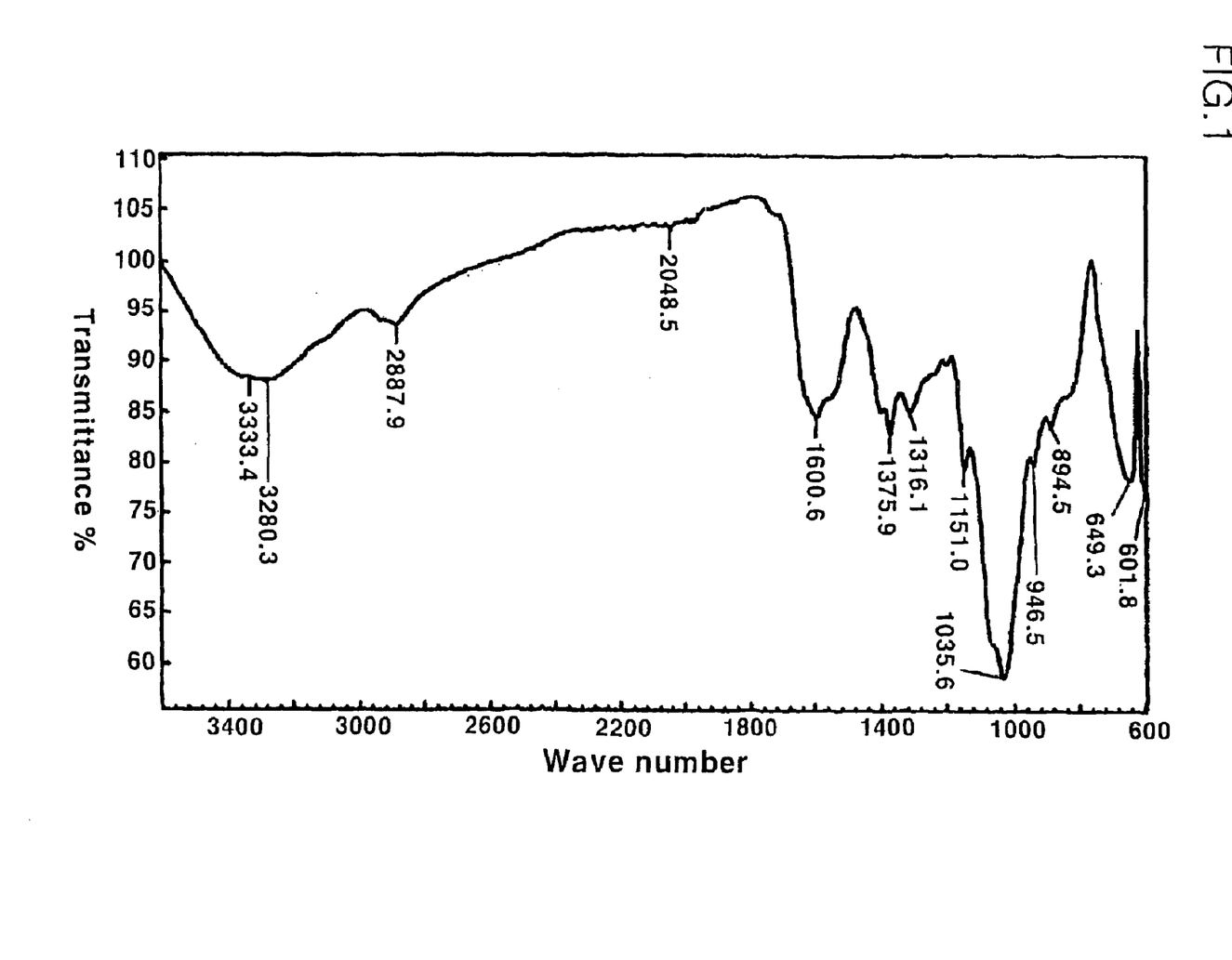
FIG. 1 is a spectrum of infrared spectroscopy for Sample A of Table 2 in example 3.
Figure 2:
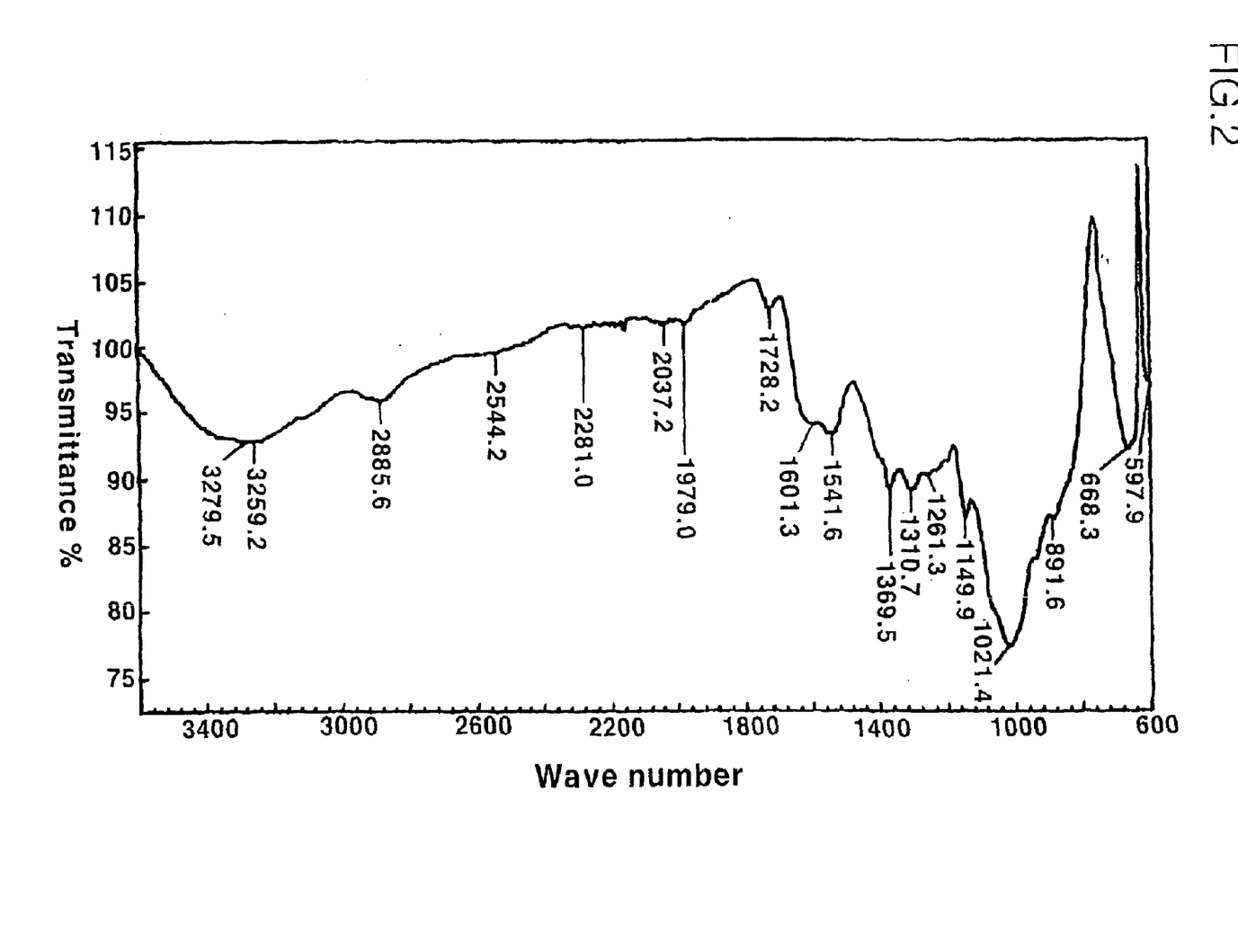
FIG. 2 is a spectrum of infrared spectroscopy for Sample B of Table 2 in example 3.
Figure 3:
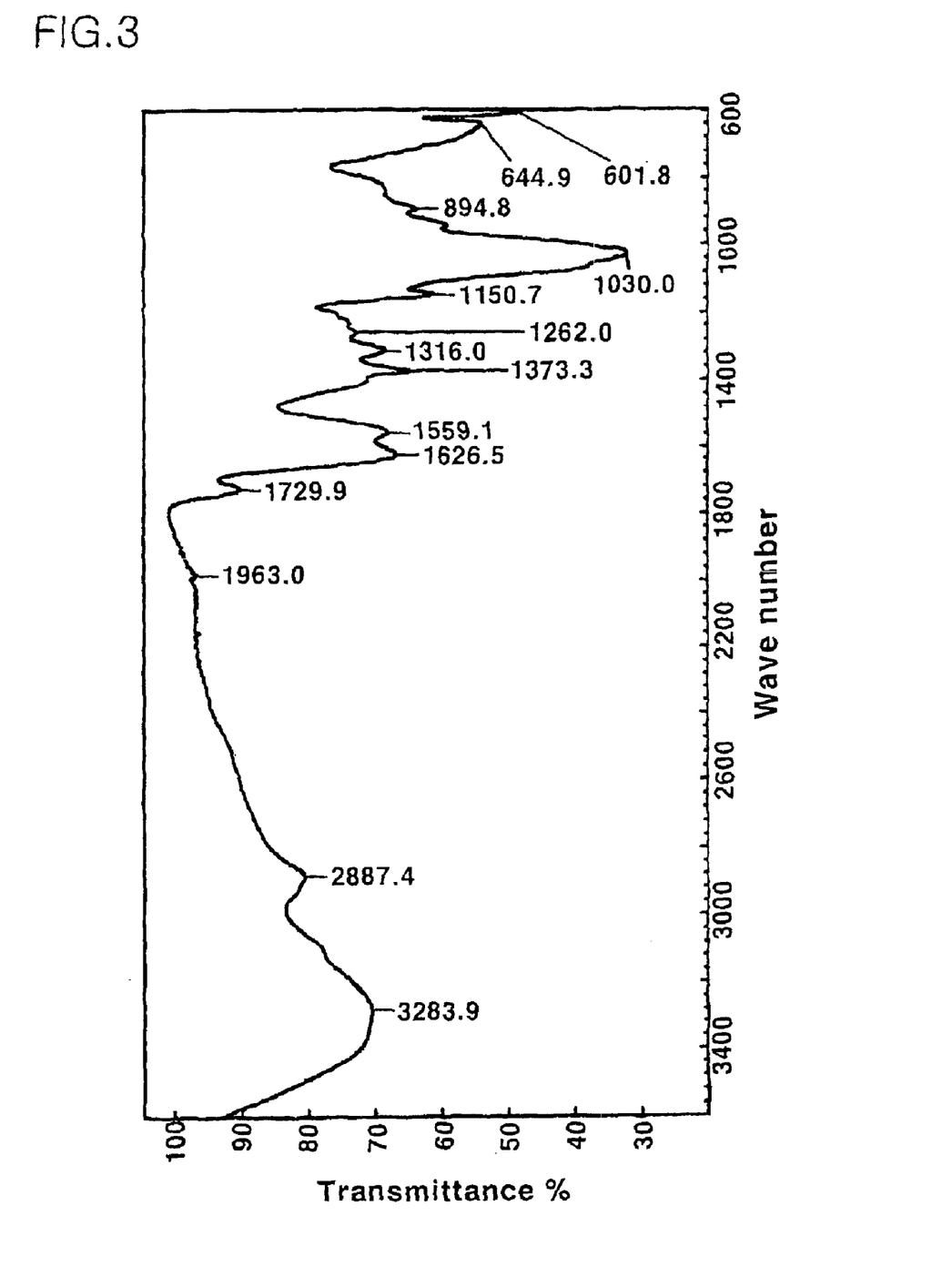
FIG. 3 is a spectrum of infrared spectroscopy for Sample C of Table 2 in example 3.
Figure 4:
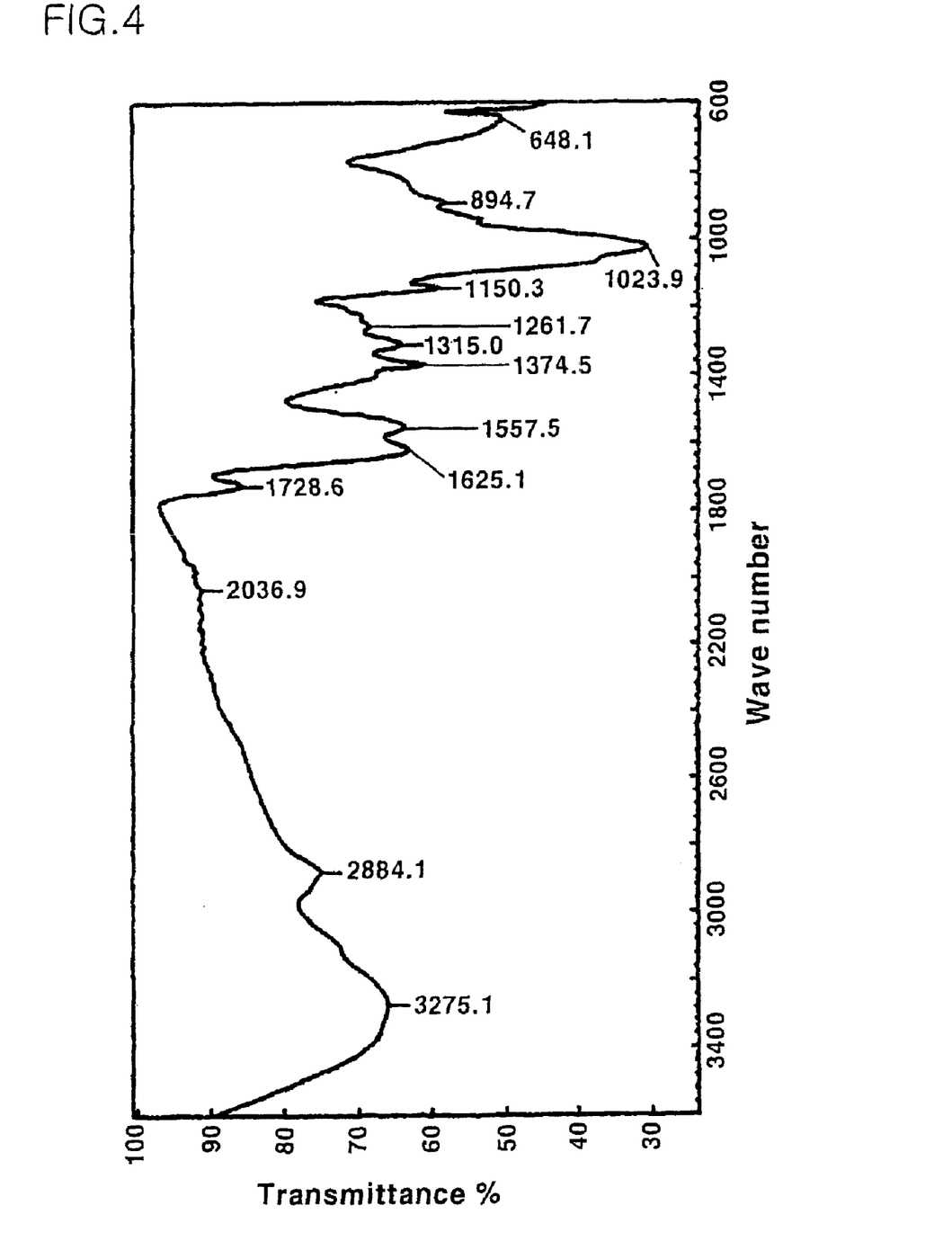
FIG. 4 is a spectrum of infrared spectroscopy for Sample D of Table 2 in example 3.
Figure 5:
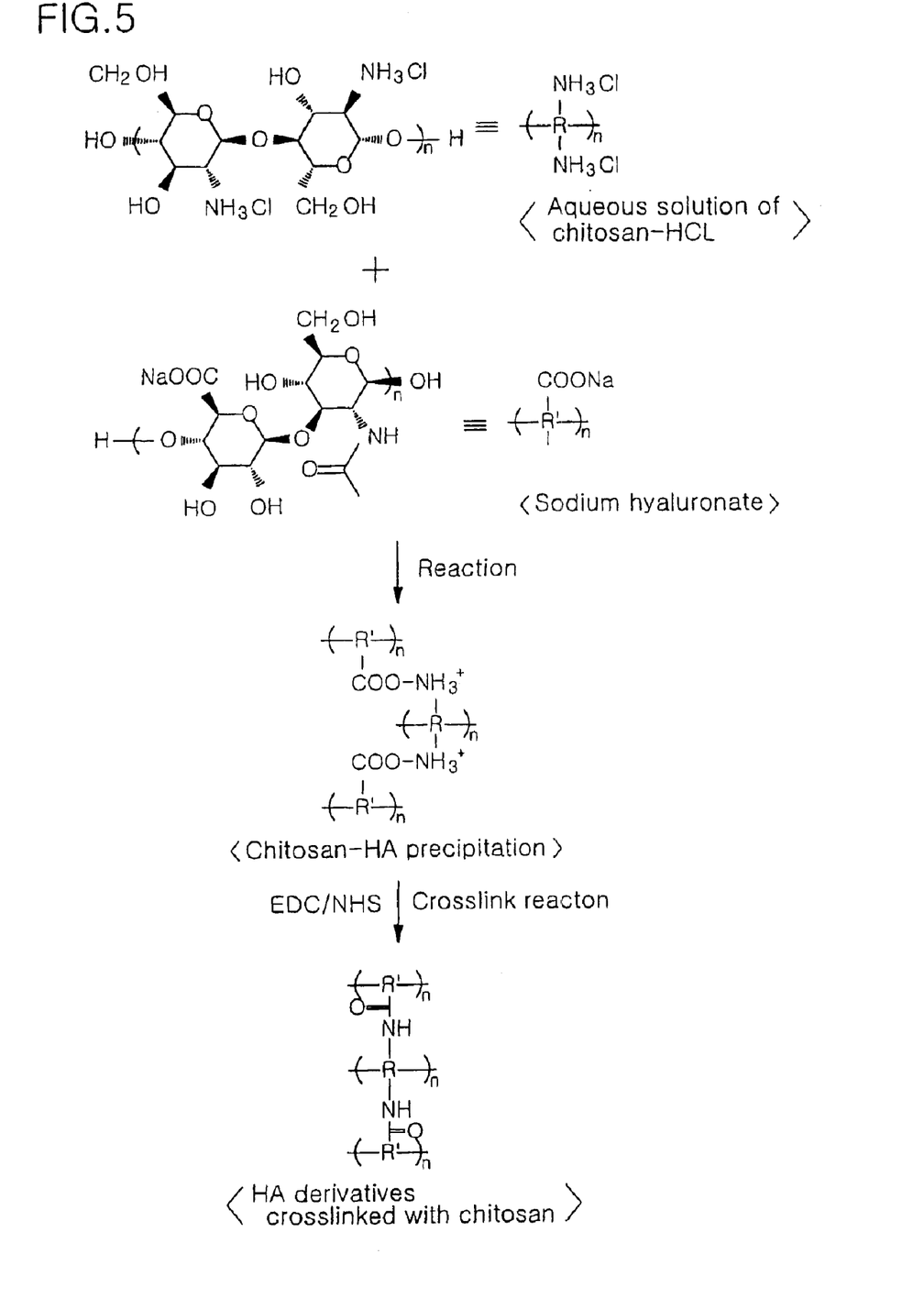
FIG. 5 is diagrammatic presentation of structure and synthesis procedure for hyaluronic acid derivative crosslinked with chitosan.

FIG. 5 diagrammatically shows the structure of amide derivatives of HA crosslinked with chitosan and its synthesis procedure by summarizing the above spectral analysis result and the above test result of resistance to acid and high salt concentration.

EXAMPLE 4

Preparation of Crosslinked Amide Derivatives of HA by Using Deacetylated HA

If the temperature of HA solution is raised under high or low pH condition, deacetylation is progressed along with chain decomposition so as to form quite an active amine. This amine may form amide bond with carboxyl group by the same chemistry as that of chitosan in Example 1 or 2.

Reaction was carried out for 1 to 30 hours at 25 to 50° C. with HA by using 0.2 to 10N NaOH (aq.) in order to deacetylate HA. Reaction was terminated by neutralization with HCl after which deacetylated HA was obtained by freeze-drying after dialysis. Degree of deacetylation was determined after measuring quantity of amine group formed as the result of reaction by using Roth's fluorimetric method (see Anal. Chem., 1971, 43, 880 to 882; J. Chromatogr., 1973, 83, 353 to 356; Clin. Chem. Clin. Biochem., 1976, 14, 361 to 364). Degree of deacetylation was calculated from the following equation.

Degree of deacetylation=[Conc. of amines formed]/[Conc. of repeat units of HA]×100 (%)

Concentration of repeat units of HA was obtained by quantifying carboxyl group according to the presumption that a carboxyl group exists per repeat unit of HA. Carboxyl group quantification was done by carbazole method (Anal. Biochem., 1962, 4, 330).

Degree of deacetylation became 1 to 40% as the result of reaction. The amidation reaction was carried out using deacetylated HA obtained by the above method. EDC (2.4 mg/ml) and NHS (2.9 mg/ml) were added into deacetylated HA (10 mg/ml), which was reacted for 2 hours at 25° C., then the derivatives formed were refined and vacuum dried. Water-insoluble gel was formed in yield of 51%. As test result of resistance to acid and high salt concentration for the above formed water-insoluble, crosslinked amide derivatives of HA, said amide derivatives maintained its form of undissolved status over 48 hours in 0.1N HCl aqueous solution and over 10 days in 1N NaCl aqueous solution. This test method was the same as in the above example 3.

EXAMPLE 5

Preparation of Amide Derivatives of HA Crosslinked with Deacetylated HA

In deacetylated HA, there is a lot of amine groups reactable with carboxyl group as in chitosan. Water-insoluble, amide derivatives of HA as described in example 1 utilizing these amine groups were obtained. After making mixed aqueous solution of deacetylated HA and sodium hyaluronate (mol. wt. ≥2,000,000) by amount of 0.5 mg/ml for each of both, EDC (0.2 mg/ml) and NHS (0.24 mg/ml) were added to the mixed aqueous solution to react for 2 hours at 25° C. after which the product was refined and dried. Water-insoluble gel was formed in yield of 56% as the result. As test result of resistance to acid and high salt concentration for the above formed water-insoluble, crosslinked amide derivatives of HA, said amide derivatives of HA maintained its form of undissolved status over 48 hours in 0.1N HCl aqueous solution and over 10 days in 1N NaCl aqueous solution. This test method was the same as in the above example 3.

EXAMPLE 6

Manufacturing Membrane Made of Amide Derivatives of HA Crosslinked with Chitosan 1.25 mg/ml of aqueous solution of sodium hyaluronate (mol. wt. ≦2,000,000) and 0.625 mg/ml of aqueous solution of chitosan-HCl were prepared. The above aqueous solution of sodium hyaluronate was poured into glass plate, then EDC and NHS were added to the above aqueous solution of sodium hyaluronate in various concentrations of such as Groups B, C, D and E of Table 1. After they were well mixed, the above aqueous solution of chitosan-HCl was added to the plate to produce white membrane in the plate. There could be obtained membrane made of amide derivatives of HA crosslinked with chitosan by drying the above white membrane. The following resultant percentages are the yields of amide derivatives of HA crosslinked with chitosan which were obtained for respective specimen groups: 51% from Group B-2, 63% from Group C-2, 70% from Group D-2 and 79% from Group E-2.

As test result of behavior while stirring after adding the above obtained membrane made of amide derivatives of HA crosslinked with chitosan to become 1% (w/v) in 1N NaCl aqueous solution in order to examine endurance to high salt concentration as described in example 3, the form was maintained as it was over a period of ten days.

EXAMPLE 7

Manufacturing Membrane Made of Amide Derivatives of HA Crosslinked with Chitosan 1.25 mg/ml of aqueous solution of sodium hyaluronate (mol. wt. ≦2,000,000) and 0.625 mg/ml of aqueous solution of chitosan-HCl were prepared. The above aqueous solution of sodium hyaluronate was poured into glass plate, and then EDC and NHS were added to the above aqueous solution of sodium hyaluronate in various concentrations of such as Groups B, C, D and E of Table 1. After they were well mixed, the above aqueous solution of chitosan-HCl was added to the plate to produce white membrane in the plate. There could be obtained membrane made of amide derivatives of HA crosslinked with chitosan by drying the above white membrane. The following resultant percentages are the yield of amide derivatives of HA crosslinked with chitosan which were obtained for respective specimen groups: 47% from Group B-3, 61% from Group C-3, 70% from Group D-3 and 78% from Group E-3.

As test result of behavior while stirring after adding the above obtained membrane made of amide derivatives of HA crosslinked with chitosan to become 1% (w/v) in 1N NaCl aqueous solution in order to examine endurance to high salt concentration as described in example 3, the form was maintained as it was over a period of ten days.

EXAMPLE 8

Manufacturing Bead Made of Amide Derivatives of HA Crosslinked with Chitosan A dried, amide derivatives of HA according to the above example 1 were finely ground and dispersed in water or physiological saline etc. It became bead solution of amide derivatives of HA injectable by syringe.

EXAMPLE 9

Manufacturing Bead Made of Amide Derivatives of HA Crosslinked with Chitosan A dried, amide derivatives of HA according to the above example 2 were finely ground and dispersed in water or physiological saline etc. It became bead solution of amide derivatives of HA injectable by syringe.

EXAMPLE 10

Preparing a Hydrated Gel Made of Amide Derivatives of HA Crosslinked with Chitosan 1.25 mg/ml of aqueous solution of sodium hyaluronate (mol. wt. ≦2,000,000) and 0.625 mg/ml of aqueous solution of chitosan-HCl were prepared. The above aqueous solution of chitosan-HCl was added while the above aqueous solution of sodium hyaluronate was being stirred. Hereinto EDC (0.2 to 1.2 mg/ml) and NHS (0.24 to 1.44 mg/ml) were added and reacted for 2 hours at 25° C., then the products were refined and vacuum dried. Wherefrom dried, amide derivatives of HA (200 to 700 mg) were obtained. Weights of the above dried, amide derivatives of HA were measured and then these derivatives were dipped for 48 hours in water after which the moisture smeared outside was wiped well off in order to measure water content per weight of amide derivatives of HA by measuring the increased mass. And rheological properties of gel containing water were measured by rheometer. The following measured values could be obtained as the result.

[Mass of water]/[Mass of HA derivative]=1.5 to 3.0

Storage modulus at frequency 0.01 to 0.1 Hz=50 to 300 kPa

Loss modulus at frequency 0.01 to 0.1 Hz=8 to 50 kPa

These modulus values are in range similar to that of rubber. This result coincides with the fact that the material according to the present invention is crosslinked substance and thus shows that this material may be used as implant for dermal augmentation etc. As known to those skilled in the art, high storage modulus means high elasticity while high loss modulus means high viscosity. Amide derivatives of HA of hydrated gel type having high viscoelasticity could be made by method as above.

EXAMPLE 11

Preparing Hydrated Gel Made of Amide Derivatives of HA Crosslinked with Chitosan 1.25 mg/ml of aqueous solution of sodium hyaluronate (mol. wt. ≧2,000,000) and 0.625 mg/ml of chitosan-HCl were prepared. The above aqueous solution of chitosan-HCl was added while the above aqueous solution of sodium hyaluronate was being stirred. Hereinto EDC (0.2~1.2 mg/ml) and NHS (0.24~1.44 mg/ml) were added and reacted for 2 hours at 25° C., then the products were refined and vacuum dried. Wherefrom dried, amide derivatives of HA (200~700 mg) were obtained. Weights of the above dried, amide derivatives of HA were measured and then these derivatives were dipped for 48 hours in water to produce hydrated gel type amide derivatives of HA. After moisture smeared outside of the above hydrated gel type amide derivatives of HA which had been submersed in water was wiped well off, the increased mass was measured in order to measure water content per weight of amide derivatives of HA. And rheological properties of gel containing water were measured by rheometer. The following measured values could be obtained as the result.

[Mass of water]/[Mass of HA derivative]=1.2 to 3.0

Storage modulus at frequency 0.01 to 0.1 Hz=60 to 330 kPa
Loss modulus at frequency 0.01 to 0.1 Hz=10 to 50 kPa
The hydrated gel made of amide derivatives of HA having high viscoelasticity could be made by method as above.

EXAMPLE 12

Preparing Crosslinked Amide Derivatives of Various Material Properties According to Mol. Wt. and Concentrations of HA and Chitosan and Concentrations of EDC and NHS Crosslinked amide derivatives of HA with various material properties could be prepared by combining a variety of the following parameters:

Mol. wt. of sodium hyaluronate: lower than 300,000; 300,000 to 3,000,000; higher than 3,000,000

HA conc. (mg/ml): 0.02, 0.1, 1.0, 10, and 80

Mol. wt. of chitosan represented by viscosity value of aqueous solution of chitosan (viscosity measured by Brookfield viscometer where chitosan was dissolved to be 1% conc. in aqueous solution of 1% acetic acid): low mol. wt. (20 to 200 cps); medium mol. wt. (200 to 800 cps): high mol. wt. (800 to 2000 cps)

Chitosan conc. (mg/ml): 0.005, 0.01, 0.05, 0.1, 0.5, 1.0, 5.0, 10, 20, 40, and 80

EDC conc. (mg/ml): 0.00096, 0.0048, 0.0096, 0.024, 0.048, 0.24, 0.48, 2.4, 3.84, 4.8, 19.2, 38.4, and 76.8

NHS conc. (mg/ml): 0, 0.000576, 0.001152, 0.001728, 0.00288, 0.00576, 0.00864, 0.01152, 0.0144, 0.01728, 0.0288, 0.0432, 0.0576, 0.0864, 0.144, 0.288, 0.432, 0.576, 0.864, 1.44, 2.304, 2.88, 4.32, 4.608, 5.76, 6.912, 8.64, 11.52, 23.04, 34.56, 46.08, 69.12, and 92.16

Hydrated gel type amide derivatives of HA could be made as described in Example 10 using the obtained amide derivatives of HA crosslinked with chitosan. The following measurement values could be obtained as the result of measurement of rheological properties of this gel containing water by using rheometer.

[Mass of water]/[Mass of HA derivative]=1.0 to 5.0

Storage modulus at frequency 0.01 to 0.1 Hz=20 to 410 kPa
Loss modulus at frequency 0.01 to 0.1 Hz=2 to 60 kPa

INDUSTRIAL APPLICABILITY

As water-insoluble, crosslinked amide derivatives of HA according to the present invention is very excellent in viscoelasticity, it is applicable in various uses. The crosslinked amide derivatives of HA according to the invention may be diversely used for prevention of adhesion after surgical operation, correction of facial wrinkles, dermal augmentation, tissue engineering, osteoarthritic viscosupplement etc.

Particularly, the present invention have features that faster reaction rate and higher yield can be obtained by reacting the polycationic polymer or oligomer having two or more amine groups and the above HA, which are close to each other by electrostatic attraction between the amine group and carboxyl group. Because the polycationic polymer or oligomer having two or more amine groups and the HA do not form the ionic bonds but form the covalent bonds by amidation reaction, the crosslinked amide derivatives of HA according to the present invention are bio-materials which resist conditions of living bodies, i.e., high salt concentrations, low pH etc. And those may be said to be new biomaterials having quite different properties from existing water-insoluble materials through HA crosslinked by using EDC. Features of water-insoluble, crosslinked amide derivatives of HA according to the present invention are that these are new bio-materials having overcome demerit of existing HA derivatives to be easily decomposed in living body and easily dissolved under harsh condition such as acidic condition etc. as well as these are biologically acceptable material of,excellent property showing high viscoelasticity.

More particularly, the present invention provides manufacturing method of water-insoluble, crosslinked amide derivatives of HA characterized in the method comprising steps of; mixing the HA aqueous solution with the polymer or oligomer aqueous solution having two or more amine groups to induce electrostatic attraction between the HA and the polymer or oligomer; reacting the two functional groups existing close to each other, i.e. carboxylate of the HA and amine group of the polymer or oligomer to produce water-insoluble bio-materials; washing by water and acid solution etc.; isolating the refined material; and drying the material. The manufacturing method according to the present invention has some features of easy reaction, simple separation process and no needs of toxic, organic solvent.

Whereas present invention has been minutely explained as above highlighting concrete examples described above, it is manifest to this enterpriser that their various transformations-modifications are possible within category of present invention and within range of its techn(olog)ical philosophy and so it is also fair-proper that such transformations-modifications belong to range of my appended patent claim.

What is claimed is:

1. A method for manufacturing water-insoluble, hyaluronic acid or hyaluronate salts crosslinked with a polymer or oligomer selected from the group consisting of chitosan, deacetylated hyaluronic acid and deacetylated hyaluronate salts, having two or more reactable amine groups which can accept protons, said method comprising the step of: reacting said polymer or oligomer with hyaluronic acid or its hyaluronate salts through an amidation reaction in the presence of a carboxyl group activating agent and said activating agent may optionally include an auxiliary agent.

2. The method of claim 1, wherein the polymer or oligomer having amine groups which can accept protons is selected such that it is positively charged under acidic or neutral conditions and wherein the amidation reaction is promoted by the electrostatic attraction between the positively charged amine groups of said polymer or oligomer and the carboxyl groups of said hyaluronic acid or hyaluronate salts.

3. The method of claim 2, wherein said amidation reaction is carried out under acidic or neutral conditions.

4. The method of claim 1 or 2, wherein the ratio of the carboxyl groups of the hyaluronic acid or hyaluronate salts versus the amine groups of the polycationic polymer or oligomer is in the range of 1:0.01 to 100 in the reaction mixture.

5. The method of claim 1 or 2, wherein the molecular weight of hyaluronic acid or hyaluronate salts is in the range of 10,000 to 10,000,000 and the concentration of those is in the range of 0.01 mg/ml to 100 mg/ml.

6. The method of claim 1, wherein carbodiimide is being used as carboxyl group activating agent.

7. The method of claim 6, wherein said carbodiimide is 1-ethyl-3-(3-dimethylaminopropyl)carbodiimide hydrochloride (EDC) while N-hydroxysuccinimide(NHS) is added optionally as an auxiliary agent to the amidation reaction.

8. The method of claim 6, wherein said carbodiimide is selected from the group consisting of 1-alkyl-3-(3-dimethylaminopropyl) carbodiimides having a structure similar to EDC, 1-ethyl-3-(3-(trimethylammonio)propyl) carbodiimide (ETC) or 1-cyclohexyl-3-(2-morpholinoethyl) carbodiimide (CMC) while a compound selected from the group consisting of N-hydroxysuccinimide (NHS), 1-hydroxybenzotriazole (HOBt), 3,4-dihydro-3-hydroxy-4-oxy-1,2,3-benzotriazine (HOOBt), 1-hydroxy-7-azabenzotriazole (HOAt), N-hydroxysulfosuccinimide (Sulfo-NHS) is added optionally as auxiliary agent to the amidation reaction.

9. The method of claim 7, wherein said EDC is added in the range of 0.0001 to 100 mg/ml and said NHS is added in the range of 0–100 mg/ml.

10. The water-insoluble hyaluronic acid or hyaluronate salts crosslinked with a polymer or oligomer manufactured by the method of claim 1.

11. The water-insoluble hyaluronic acid or hyaluronate salts crosslinked with a polymer or oligomer manufactured by the method of claim 2.

12. The water-insoluble hyaluronic acid or hyaluronate salts crosslinked with a polymer or oligomer manufactured by the method of claim 4.

13. The water-insoluble hyaluronic acid or hyaluronate salts crosslinked with a polymer or oligomer manufactured by the method of claim 3.

14. The water-insoluble hyaluronic acid or hyaluronate salts crosslinked with a polymer or oligomer manufactured by the method of claim 5.

15. The water-insoluble hyaluronic acid or hyaluronate salts crosslinked with a polymer or oligomer manufactured by the method of claim 6.

16. The water-insoluble hyaluronic acid or hyaluronate salts crosslinked with a polymer or oligomer manufactured by the method of claim 7.

17. The water-insoluble hyaluronic acid or hyaluronate salts crosslinked with a polymer or oligomer manufactured by the method of claim 8.

18. The water-insoluble hyaluronic acid or hyaluronate salts crosslinked with a polymer or oligomer manufactured by the method of claim 9.

19. The water-insoluble hyaluronic acid or hyaluronate salts crosslinked with a polymer or oligomer of claim 10, wherein those have form of gel, membrane, bead or mesh.

* * * * *